United States Patent
Daum

(10) Patent No.: US 6,408,289 B1
(45) Date of Patent: *Jun. 18, 2002

(54) SHAPEABLE ELASTIC BODY WITH MASTER UNIT AND METHOD OF CONTROLLING

(75) Inventor: Wolfgang Rudolf Daum, Schwerin (DE)

(73) Assignee: MRI Devices Daum GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/929,496

(22) Filed: Sep. 15, 1997

Related U.S. Application Data

(63) Continuation of application No. 08/250,669, filed on May 27, 1994, now abandoned.

(30) Foreign Application Priority Data

Jun. 11, 1993 (EP) .............................. 93109348

(51) Int. Cl.⁷ ................................................. G06N 3/02
(52) U.S. Cl. ........................................ 706/45; 706/44
(58) Field of Search .............................. 395/80–81, 85, 395/99; 623/26; 60/527

(56) References Cited

U.S. PATENT DOCUMENTS

| | | | | |
|---|---|---|---|---|
| 4,650,492 A | * | 3/1987 | Barkhordar et al. | 623/24 |
| 4,716,731 A | * | 1/1988 | Sakai et al. | 60/527 |
| 4,776,852 A | * | 10/1988 | Rubic | 623/26 |
| 4,792,173 A | | 12/1988 | Wilson | |
| 5,021,064 A | * | 6/1991 | Caines | 623/26 |
| 5,035,530 A | * | 7/1991 | Fukuda et al. | 403/404 |
| 5,172,551 A | * | 12/1992 | Nakajima et al. | 60/527 |
| 5,329,212 A | * | 7/1994 | Feigleson | 318/16 |
| 5,432,395 A | * | 7/1995 | Grahn | 310/328 |
| 5,619,177 A | * | 4/1997 | Johnson et al. | 337/140 |
| 5,697,285 A | * | 12/1997 | Nappi et al. | 91/519 |
| 5,788,425 A | * | 8/1998 | Skow et al. | 406/88 |
| 5,810,170 A | * | 9/1998 | Alvite | 206/714 |
| 5,813,406 A | * | 9/1998 | Kramer et al. | 128/782 |

FOREIGN PATENT DOCUMENTS

GB      2013617      8/1979

OTHER PUBLICATIONS

Reynaerts, D., and H. Van Brussel. "Development of a SMA high performance robotic actuator." ICAR 1991 Fifth International Conf. on Advanced Robotics, Jun. 1991.*

Ino, S., et al., "A basic study on the tactile display for tele–presence." Proceedings of the IEEE Intl. Workshop on Robot and Human Communication, Sep. 1992.*

Hunter, I., and S. Lafontaine. "A comparison of muscle with artificial actuators." IEEE Solid–State Sensor and Actuator Workshop, May 1992.*

Proceedings 1990 IEEE International Conference on Robotics and Automation, May 1990, IEEE Computer Society Fukuda et al: Distributed type of Underwater Mobile Robotic Mechanism pp. 1316 to 1321.

* cited by examiner

*Primary Examiner*—Mark R. Powell
*Assistant Examiner*—Wilbert L. Starks, Jr.
(74) *Attorney, Agent, or Firm*—Saliwanchik, Lloyd & Saliwanchik

(57) ABSTRACT

An elastic robot body in which a number of actuators are integrated. If the actuators are triggered individually or in groups, they exercise a force on the material of the body, so that the latter changes its shape. Integrated sensors or switches measure the momentary position of the body. An imitation hand, comprising such a body, can move its sections in a human fashion.

21 Claims, 17 Drawing Sheets

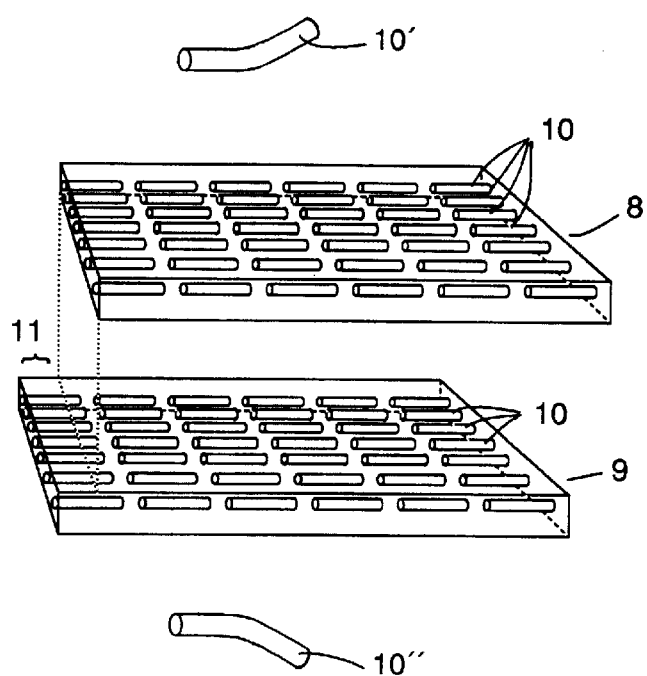
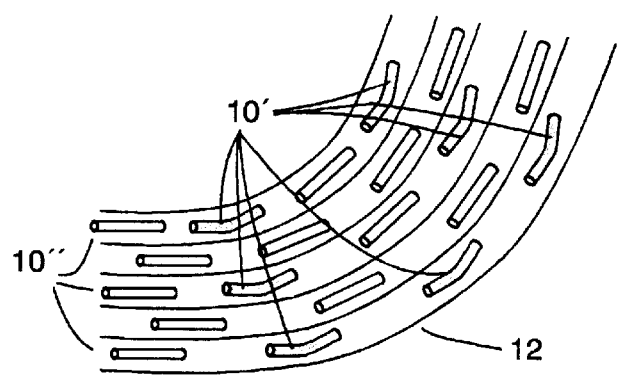
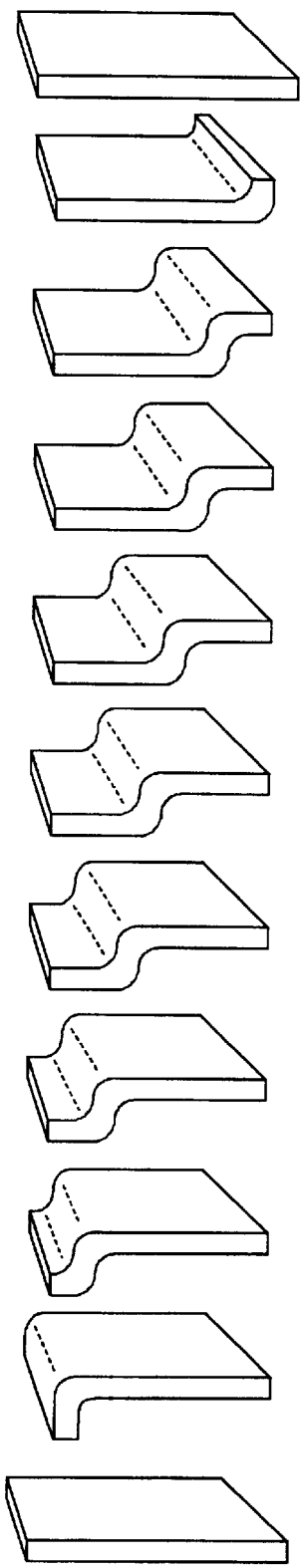
Fig. 3a
Fig. 3b
Fig. 3c

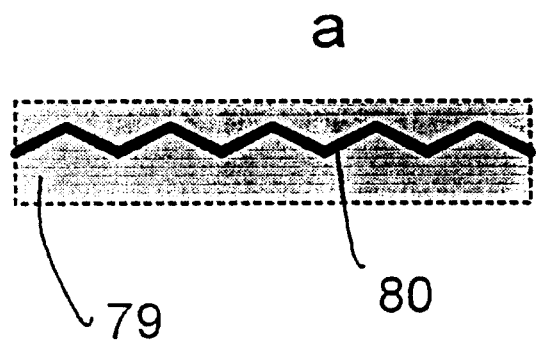
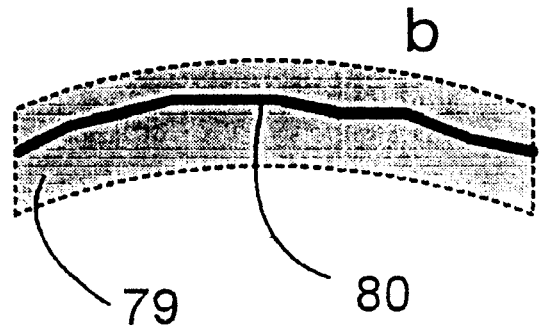
Fig. 23a
Fig. 23b
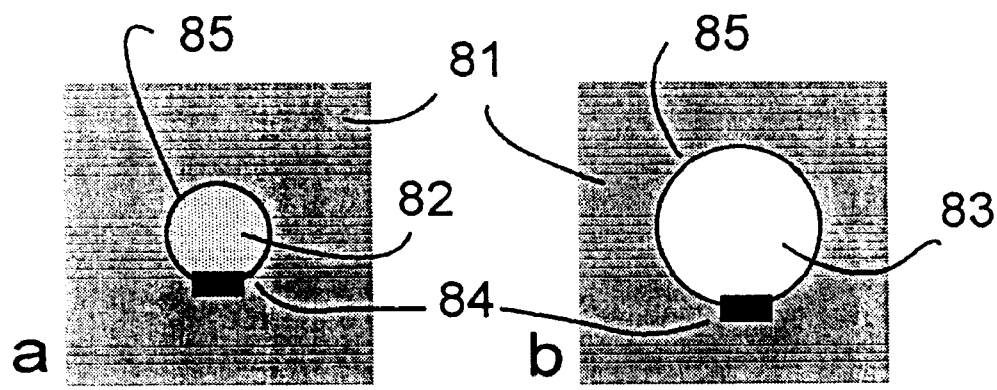
Fig. 24a
Fig. 24b

SHAPEABLE ELASTIC BODY WITH MASTER UNIT AND METHOD OF CONTROLLING

CROSS-REFERENCE TO RELATED APPLICATIONS

This application is a file wrapper continuation of U.S. patent application Ser. No. 08/250,669, filed May 27, 1994, now abandoned.

TECHNICAL FIELD

The invention involves an elastic body used in robotic applications.

BACKGROUND OF THE INVENTION

At present movement sequences of technical appliances are operated by individual or several motors or actuators of diverse design. Alterations to the movement are obtained by the addition of e.g. gear systems, levers or pulleys, the movement sequences of which are determined during the construction stage and which can subsequently be changed only by reassembly. The movement sequence is determined by the construction.

In contrast to techniques designed by man, movements in nature are produced e.g. by muscles. These comprise a number of cells which can contract. In a working muscle, it is rare for all muscle cells to be active at the same time, but only those cells and as many as are required to execute the movement. As a result, a muscle is much more flexible and can also execute unpredicted movements. For the movement sequences are not determined in advance by the construction, but learned. The movement mechanism of a muscle works on a redundant principle, i.e. if some muscle cells fail, others will always contract in their place so that the overall muscle movement achieved is again correct.

If mechanical elements similar to muscles were available, it would be possible to produce a whole range of new appliances, such as imitation human limbs. Mechanical elements with movements determined not by their construction but only by a computer program which controls them, would solve many technical problems. This would apply especially if the task required of the mechanical element or of the appliance to which the element belongs were to change.

The demand for redundancy in technical systems is at present met by multiple installation in small numbers of the same constructional elements in these appliances. In that case, the elements themselves are not redundant. It would accordingly be desirable to have mechanical elements which are self-redundant.

In computer engineering algorithms have now been developed which are self-learning. The conversion of such algorithms into the mechanical world makes particular sense if the movements which can be executed by the appliances are not rigidly determined by their construction, but flexible.

Movement sequences of technical appliances are now determined by means of individual or small quantities of sensors. These sensors are located at important positions for the special control sequence of a special construction. Since the movement sequences are determined by the construction, the low number of fixed position sensors is adequate to register the movements.

That would not however be the case if one had mechanical elements the movements of which were not determined by the construction, but were flexible and determined by a computer algorithm. Registration of the momentary position and movement of such elements with conventional means would prove difficult if not possible and could even corrupt the character of the elements. For such an element, it would therefore be desirable to have a sensor system which could register all changes of shape and movement.

Man has created the technical environment in which he lives in such a way that his limbs allow him to act in an optimum fashion. Robots which take over work from man in this environment can work particularly rationally if they have a humanoid construction and move accordingly. For that reason, robot hands in particular must correspond to human hands.

Goal of the invention is to create an elastic body which can change its shape almost continually, which is controlled by computer algorithms and serves as a mechanical element, e.g. for generating power and motion. In that respect, the invention is also aimed at creating a type of organic body to the effect that the latter can be controlled by self-learning algorithms. The aim is furthermore to measure the change in shape of such a self-shaping element.

A further aim of this invention is to create robot hands with a master-slave control with their own integrated drive systems and with an elastic construction which makes them pleasant to humans.

A further goal is to achieve elastic robot limbs for the use in technical robots, toys or film-, show- and amusement-puppets and to create a master-unit for inserting the desired movements of such robots and puppets and to create a method of controlling. See GB-A-2,013,617 for further background. For more background understanding, see 'Proceeding 1990 IEEE International Conference on Robotics and Automation', Mai 1990, IEEE Computer Society, Fukuda et al.: Distributed Type of Actuators by Sma and its Application to Underwater Mobile Robotic Mechanism, pages 1316 to 1321.

A further aim of the invention is to provide a glove-device for inserting the movements of the human hand into the computer.

A further aim of the invention is to provide a method for controlling a robot hand with said new glove-device.

Although technical appliances operated by a number of actuators are known, such as that represented in DE 29 15 313, the actuators of that appliance are not however integrated in elastic material so that a number of non-predetermined movements can be executed but only those determined by the construction.

Although technical appliances which feature elastic bodies as an integral component are known, such as that represented in DE 40 33 089, they are not operated by a number of individually or group-triggered actuators. These too do not permit a variety of non-predetermined movements.

Although remote-control imitation hands are known, such as that represented in WO 90/04370, the number of control elements is so limited that these hands can execute only movements which on the one hand are predetermined by the construction and are on the other hand very abrupt. There is no measurement of the momentary position of the limb sections.

BRIEF DESCRIPTION OF THE DRAWINGS

The aims of this invention are solved by this invention. These are elucidated on the basis of the following schematic figures:

FIG. 3a is a combination of two matrices with memory wires acting in different directions;

FIG. 3b is a cross-section through five matrices when bent;

FIG. 3c is a series of perspective views of a movement sequence of a panel-shaped elastic body;

FIGS. 23a and b are cross-sectional views of a portion of an elastic body bent and unbent, respectively; and FIGS. 24a and b are cross-sectional views of another actuator in actuated and unactuated positions.

DETAILED DESCRIPTION OF THE PREFERRED EMBODIMENTS

Figure 1A:
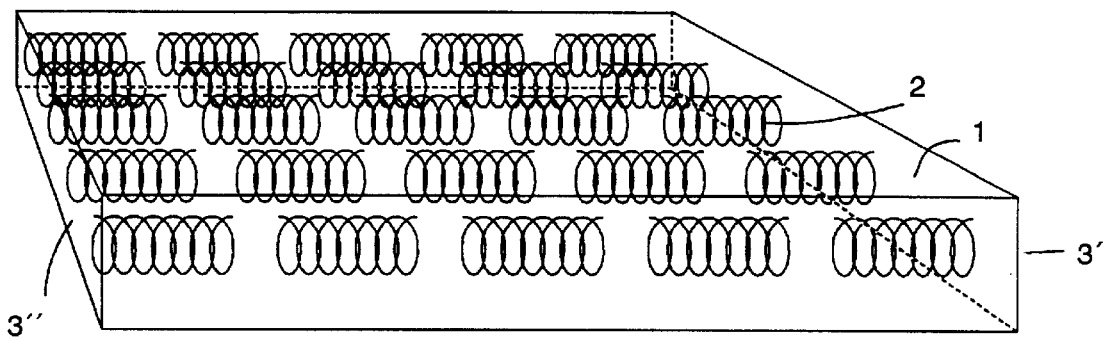
FIG. 1a is a perspective view of a panel-shaped elastic body with spirals made of memory material as actuators in basic condition.
Figure 1B:
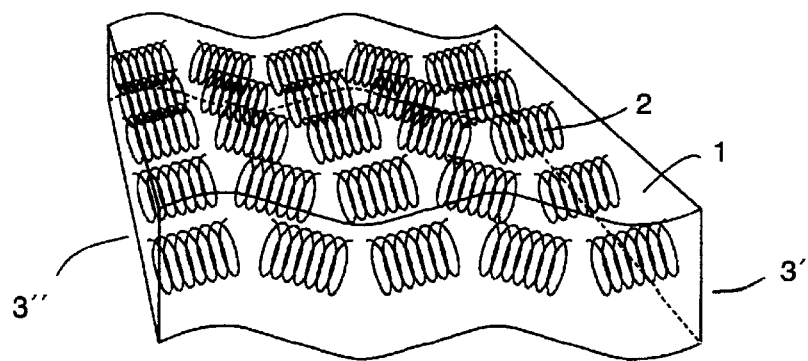
FIG. 1b is a figure like FIG. 1a except showing actuator when actuated.

FIG. 1 shows an elastic body (1) made for example of silicone rubber. That body has integrated spiral springs (2), which can contract in accordance with a mechanism described in detail below. Here they are called actuators as they execute a movement or action when in operation. FIG. 1a shows them in their unactuated basic condition. Actuated, in FIG. 1b, they contract and thus contract the body, the shape of the body (1) changes, it undulates and surfaces (3) and (4) converge.

Memory metals, such as certain titanium-nickel alloys, change their external shape at certain temperatures owing to phase conversion. The spirals shown in FIGS. 1a and b are made of such a material. The actuated condition is achieved by a change in temperature.

Figure 2A:
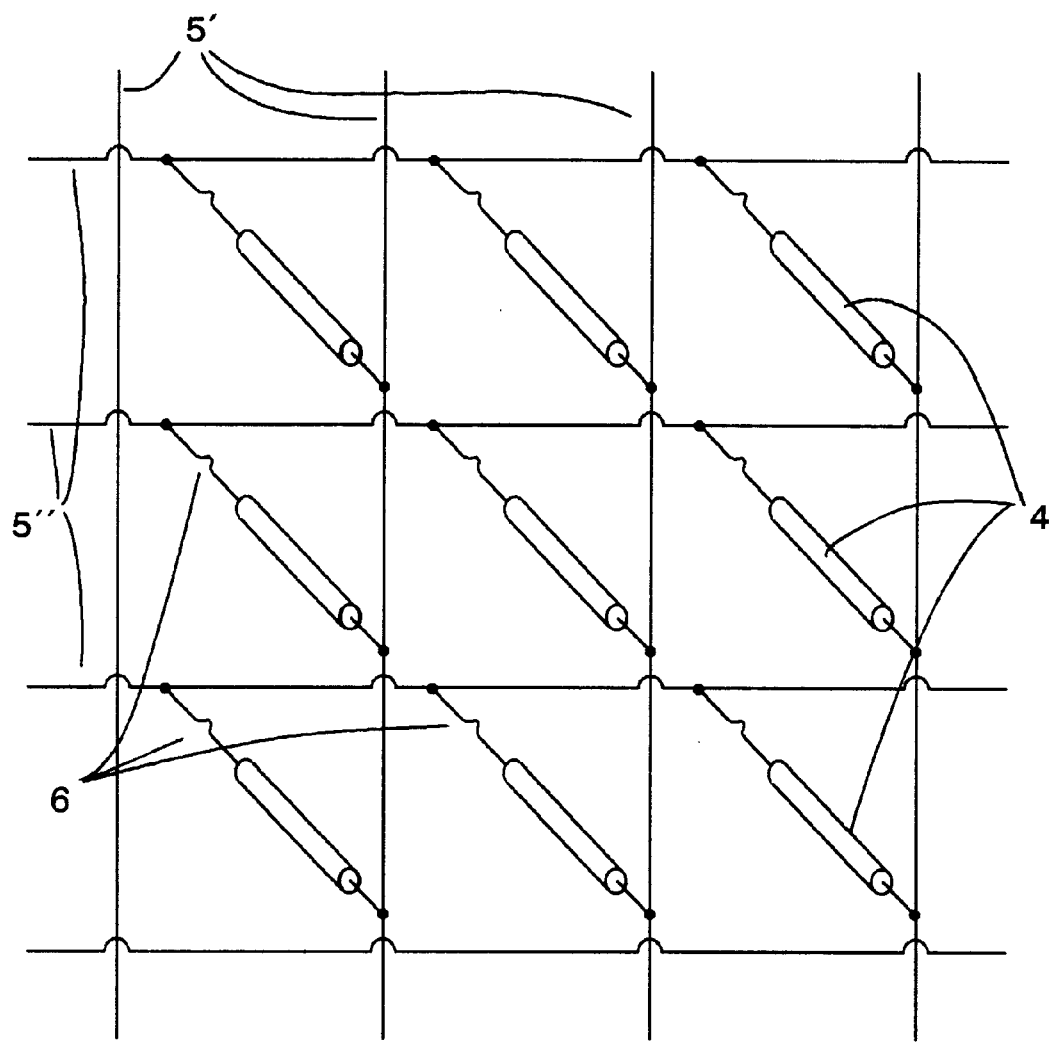
FIG. 2a is an arrangement of memory wires to form a two-dimensional matrix.
Figure 2B:
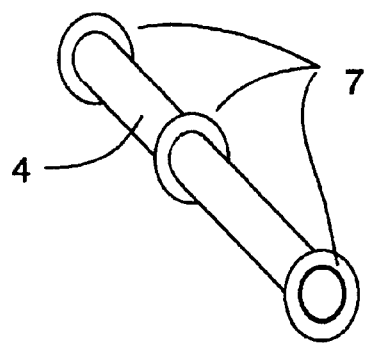
FIG. 2b is a memory wire with holder.

FIG. 2a shows a part of a two-dimensional force element matrix of memory wires. By selecting the correct control leads (5') and (5"), the wires can be individually triggered and directly heated. The resistance of control leads (5') and (5") is calculated so that only the memory wires are heated. Indirect heating is however also conceivable. Tension release devices (6) make the matrix flexible for movements. By means of the holders or ribs (7), designed for instance as rings, FIG. 2b, the memory wires (4) can be held in position in the elastic material of the body when the shape changes. Holders 7 engage the elastic material to hold the actuators fixed in position in the material when actuating.

FIGS. 3a–c illustrates how a virtually constant movement can be executed with a single-actuator trigger. As in all the other figures, this does not show the control leads and holders.

Several of the two-dimensional matrices shown in FIG. 2a are integrated in a rubber elastic body. The planes formed by the matrices are offset in relation to each other by approximately one half wire length (11) in each case. FIG. 3a elucidates this on the example of two layers (8) and (9). The planes need not have any real, but only a mentally arranging character. Representative of all elements in one plane, the direction in which the actuators of planes (8) and (9) act is shown on the example of the curve of wires (10') and 10"). FIG. 3b shows a section through a part of such a multi-layer system. Actuators (10) are operated, so that they bend and consequently bend the body (12). Operating other actuators would result in different changes in the shape of the body (12). Accordingly, continuous operation of individual or groups of actuators can achieve continuous movement at 11 consecutive intervals, as shown for example in FIG. 3c. As such memory metal parts change their shape very abruptly, the higher the number of actuators the more continuous the movement. The matrix sections shown could also interlock three-dimensionally. This results in widely varying movement sequences. All the sequences are based on the movement principle filed in this application. The great number of integrated actuators gives the elastic body redundancy, because when some actuators fail, there are always others which can be triggered in their place, so that the overall movement of the elastic body remains unchanged.

Figure 4A:
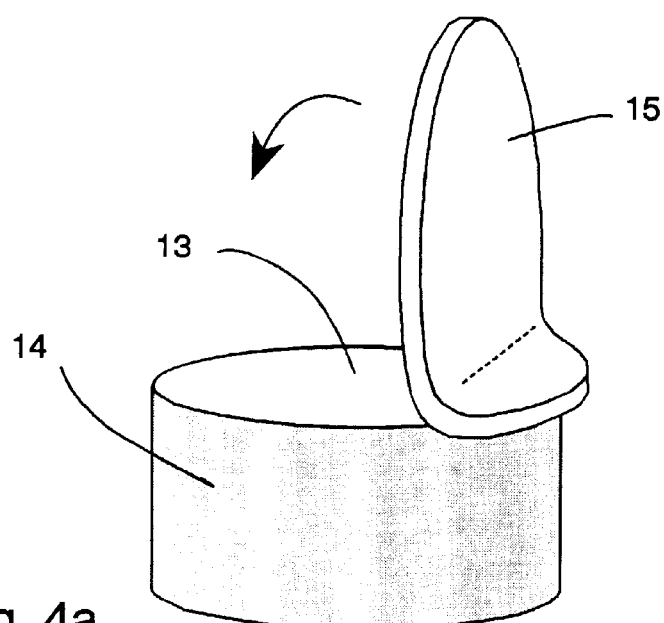
FIG. 4a is an example of a self-sealing cover, in an open position.
Figure 4B:
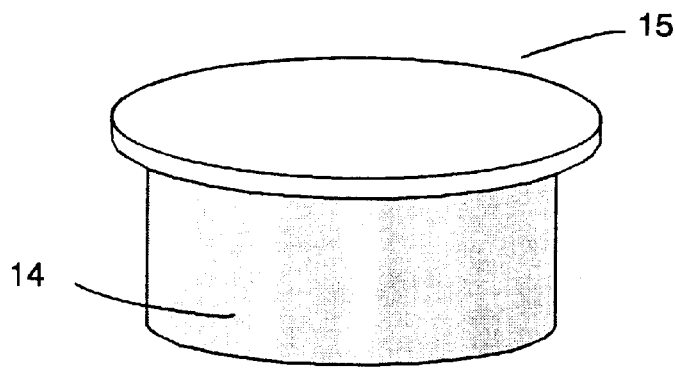
FIG. 4b is an example of a self-sealing cover, in a closed position.
Figure 4C:
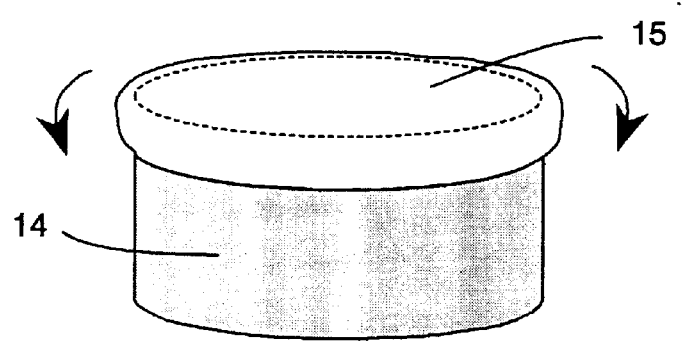
FIG. 4c is an example of a self-sealing cover, in a scaled position.

FIGS. 4a–c shows an application example. On the opening (13) of a vessel (14), there is a cover (15), which is designed as an elastic body with a number of integrated actuators. FIG. 4a shows this cover when open. By means of the movement mechanism described above, this lies down on the vessel automatically, FIG. 4b, and closes and seals the opening, FIG. 4c. This concept could be applied to any system requiring robotic closure control, such as in a radioactive or sterile environment.

Figure 5:
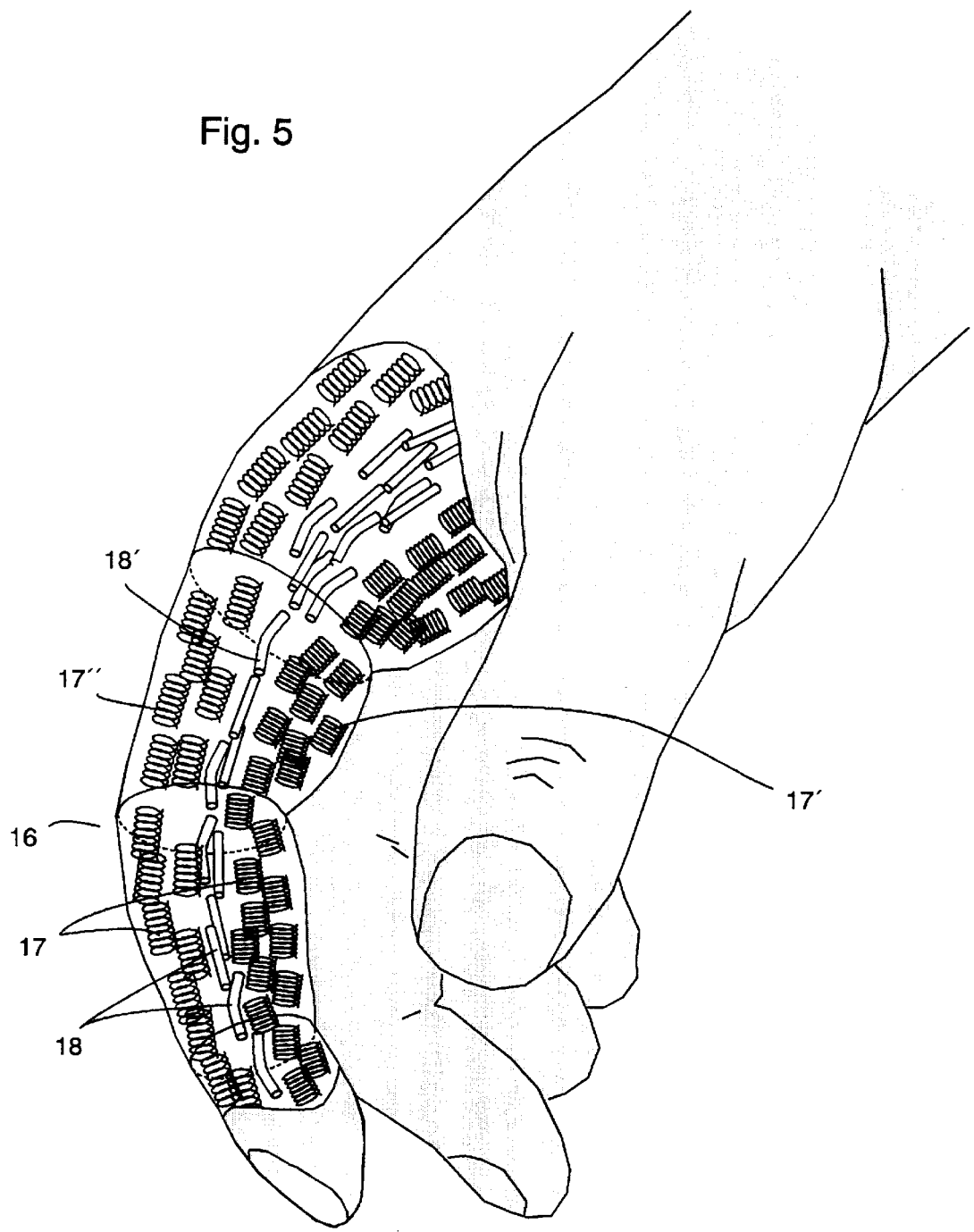
FIG. 5 is an example of an artificial hand.

Another application example of such an elastic body is the imitation of muscles. In that respect, FIG. 5 shows an artificial hand, made for instance of silicone rubber. The phantom view of the index finger (16) shows that the actuators (17) are integrated in the material without any strict order. In this case the actuators are spiral springs made of memory material (17). The figure shows an index finger in a bent position, achieved by contracting the spirals (17') of the lower side of the finger or by stretching the spirals (17") of the upper side of the finger. Any necessary supporting wires are not shown. A mode of construction composed of individual muscle tracts is also conceivable. The control or sensory elements (18) described below inform the controlling computer of the position of the finger (16).

It is not necessary to know the exact position of the actuators as shown in the example of FIG. 3. By trial and observation with e.g. graphic data evaluation, the controlling computer can learn the movements. This learning process is possible because the high number of actuators in the elastic body gives the control algorithm the possibility of selecting exactly those actuators needed to execute the desired movement. The greater the number of actuators, the greater the selection. The movements of the self-shaping element are determined not only by its construction, but in particular by the controlling computer program. It is above all because the movement sequence cannot be predetermined owing to the great number of actuators and the fact that they are integrated in an elastic material, that such a self-shaping element is suitable for control with self-learning algorithms. This fact makes such a type of elastic body similar to muscles.

Figure 6A:
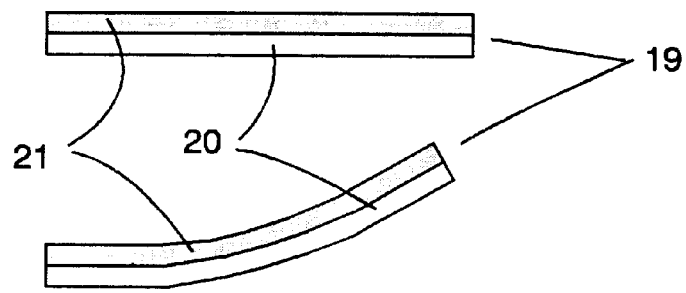
FIG. 6a is a bimetallic actuator.

The actuators can also be made of thermo-bimetals. FIG. 6a shows an example of such a bimetal (19), comprising one material (20) with a higher thermal expansion factor than the other material (21). The top section shows the thermo-bimetal (19) in an unactuated condition and therefore not bent, while in the lower section it is actuated and therefore bent.

Figure 6B:
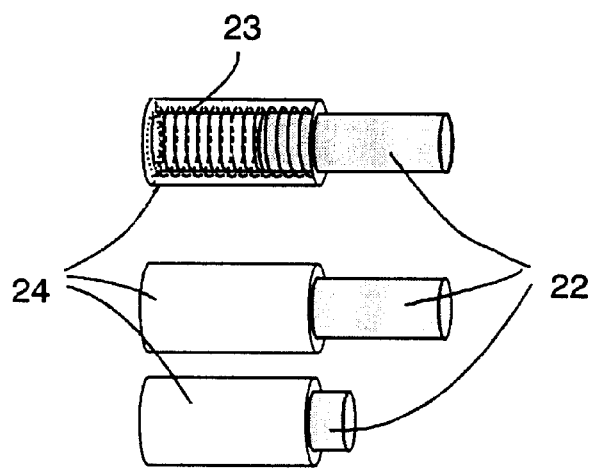
FIG. 6b is an electromagnetic actuator with inner movement.

The actuators can also work electromagnetically. FIG. 6b shows such an actuator. It comprises a magnetic core (22), which can be pressed out of and retracted into a sleeve (24) by an electromagnetic field generated by a winding (23). The lower section shows two actuators, the top one with extended, the lower with retracted core.

Figure 6C:
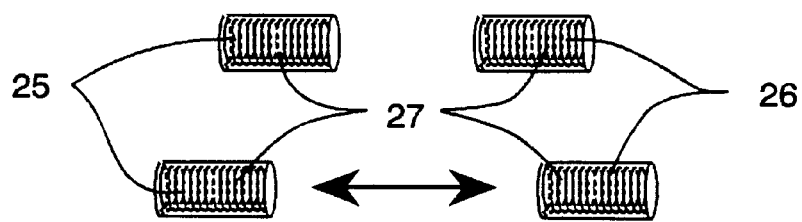
FIG. 6c are electromagnetic actuators which repel or attract each other.

Electromagnetically also means that the individual actuators do not themselves execute any inner movement, but simply repel or attract each other when in an actuated condition. The elastic material between them is stretched or compressed as a result. FIG. 6c shows two actuators (25) and (26) repelling each other (arrow) in the actuated condition in which current flows through the windings (27).

The actuators described in this application are only examples. Actuators which rotate, twist, stretch, contract, expand etc. are conceivable, as are actuators made of thin layers and films. The actuators could also work piezoelectrically or electrostrictively. Self-shaping bodies themselves could also be used as actuators.

Pressure sensors or switches can be integrated in the elastic body to ascertain the momentary position of the self-shaping element. In that case the pressure sensors measure the inner pressure of the elastic body, which can then be interpreted with the change of shape. A number of electric switches, which recognize only the states "open" or "closed" is simpler, faster and cheaper for computer control.

Figure 7A:
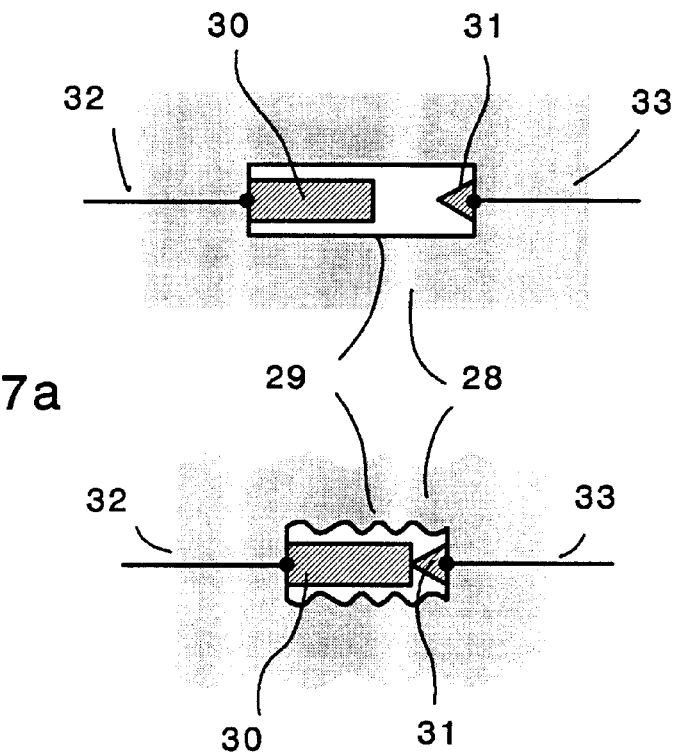
FIG. 7a is a cross-section through switches in an elastic body which respond when the body is compressed.
Figure 7B:
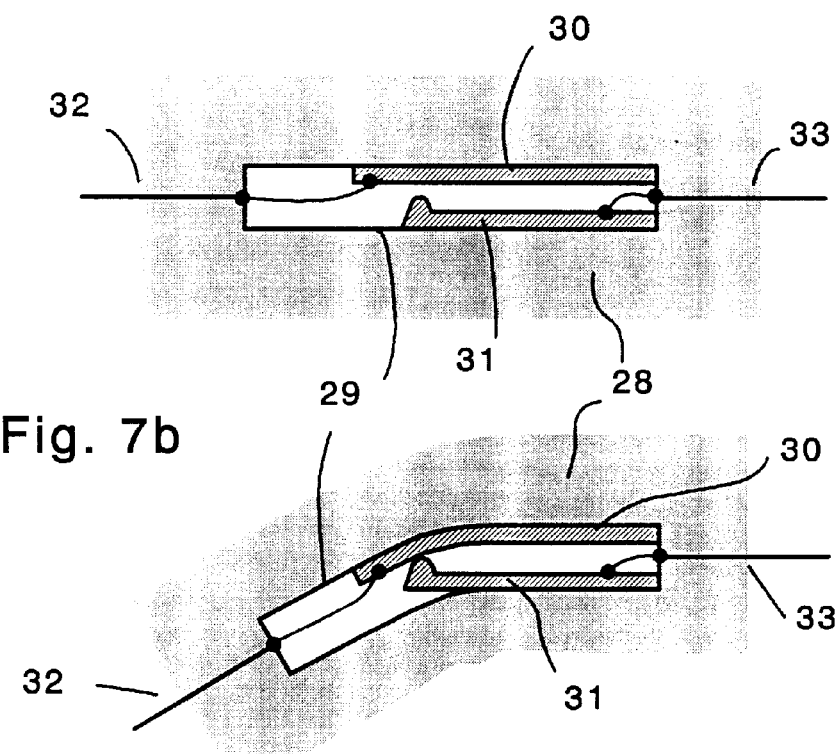
FIG. 7b is a figure like 7a except the body is bent.

FIG. 7 shows possible switch configurations which are integrated in the elastic material (28). The switches each have an elastic coating (29) and two switch contacts (30) and (31), to which the signal wires (32) and (33) are attached. In the top section of FIG. 7a, the switch is open, so that no current flows. In the lower section of FIG. 7a the elastic body (28) is compressed, the switch contacts touch so that the electric circuit closes. In FIG. 7b the contact is closed when the elastic body (28) bends—lower section of figure. The switches (18) shown in FIG. 5 could be constructed like those shown in FIG. 7b. The closed switches (18') would then provide information about the curve of the finger (16) or the change in shape of the elastic body. The greater the number of switches, the more accurate the result. The correlation of the switch states with the curve of the finger (16) can be executed by a self-learning computer algorithm.

The great number of switches or sensors means that the position of such a body can be determined by self-learning associative algorithms. Similar to the situation of a human being, for instance, who in the case of fast but familiar movements no longer has to think about the individual movement stages, here too only a few exposed switch positions would have to be determined in order to recognize the position of the body by association. The large number of actuators and sensors thus make the mechanism more organic.

Figure 8A:
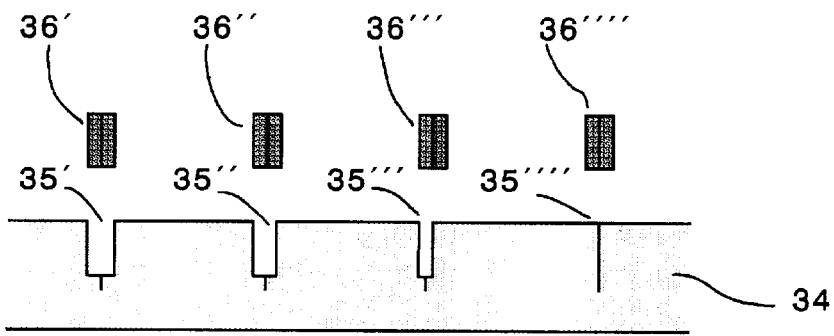
FIGS. 8a–f use cross-section through switches in an elastic body which respond when the body is bent.

FIGS. 8a–f shows a cross-section of a different switch construction. FIG. 8a shows the elastic body (34) with three material notches (35'), (35"), 35"') and the simple cut into the material ( 35""). In contrast to the following FIGS. 8b–8f, the switches (36'), (36"), (36"') and (36""), each composed of two switch contacts, have not yet been inserted into the elastic body (34) in FIG. 8a to allow clearer representation.

Figure 8B:
Figure 8C:
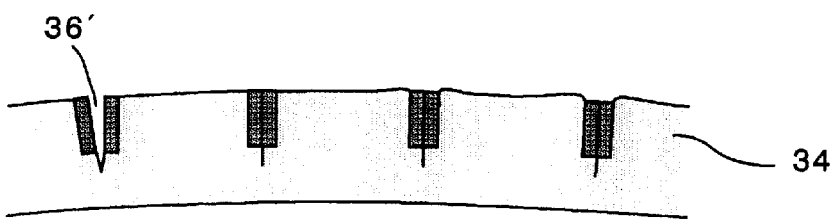
Figure 8D:
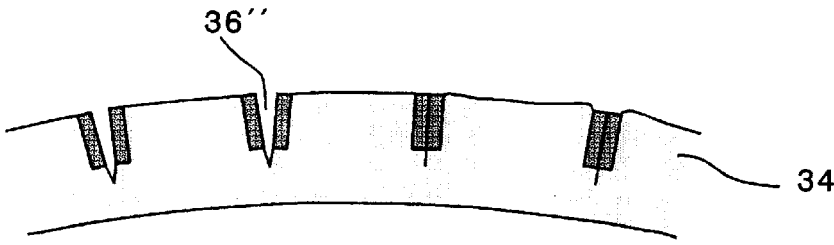
Figure 8E:
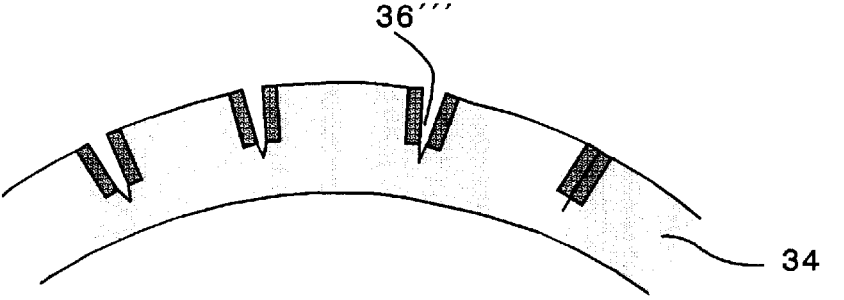
Figure 8F:
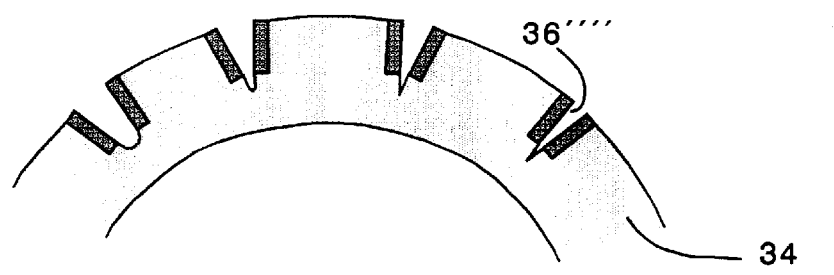

In the basic unbent condition of the elastic body (34), all contacts (36) are closed, FIG. 8b. If the elastic body (34) is bent, these contacts open. Owing to the different sized material notches and the geometric curve sequence shown in FIG. 8, this happens successively. In FIG. 8c (36'), in FIG. 8d (36"), in FIG. 8e (36"') and in FIG. 8f (36""). These consecutive changes in the switch positions can be interpreted as the change in shape—bend—of elastic body (34) in a computer program.

Evaluating this number of switches is particularly simple thanks to the digital character of the switches, which does not call for any complicated adjustment of the measured values (temperature, time, hysteresis) or analog-digital converter.

Figure 9:
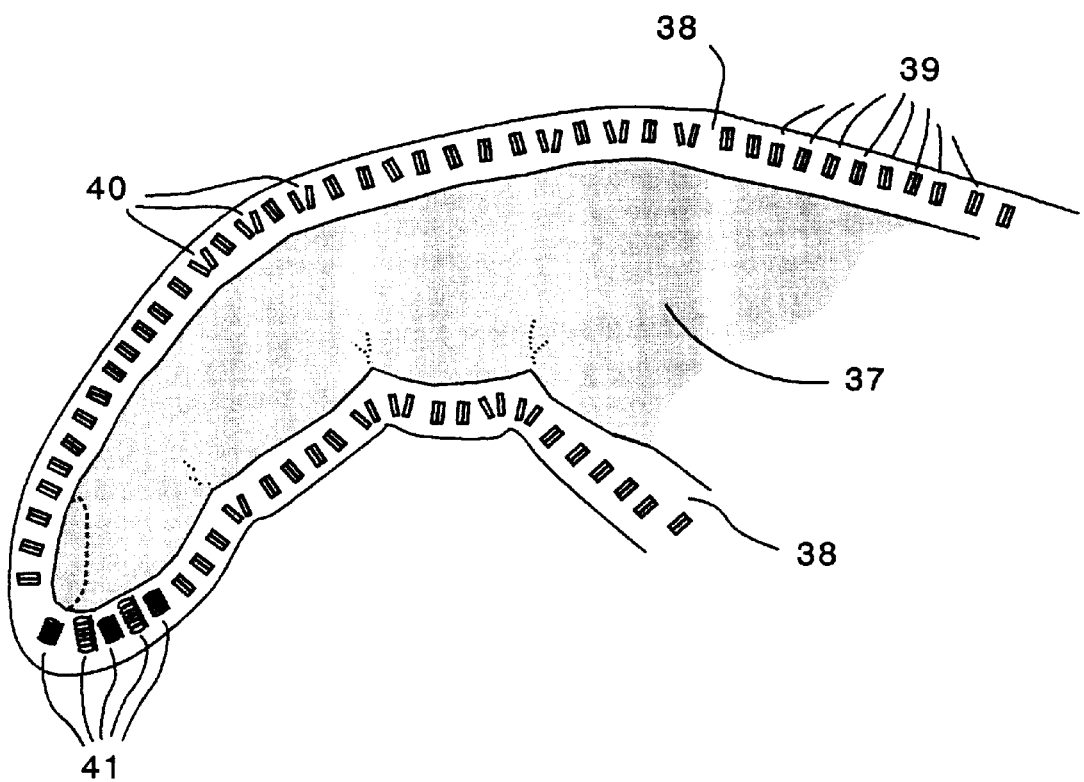
FIG. 9 is a cross-section through a finger part of a data glove comprising an elastic body with a number of switches with a structure identical to those in FIG. 8.

The principle of the switch configuration shown in FIG. 8 can be used for a data glove. For purposes of elucidation, FIG. 9 shows a cross-section of a finger part of such a glove. The human finger (37) is inserted in this finger part, which comprises an elastic body (38), in which a number of switches (39) are integrated. Depending on the bend of the human finger (37), the shape of the elastic body (38) changes, so that the switches are opened, as shown for instance in (40).

The movement of the human extremities can be registered in this way. This switch data can be used, for instance, to control the robot hand of FIG. 5. The robot hand could also wear a data glove with exactly identical construction. By comparing all the switch positions of both data gloves, the computer can move the robot hand so that it executes the same movements as the human hand. The greater the number of switches, the more exactly it corresponds.

For controlling a robot limb, e.g. a robot hand, there could be a second elastic body comprising the same shape as said robot limb. In this said second elastic body there are inserted a plurality of narrowly spaced sensors or switches which will change their state when the body is shaped to a new shape. The operator can now shape the said second elastic body and a computer software sill move said first robot limb accordingly.

The use of a second similar elastic body for master-slave control is also conceivable.

Figure 10A:
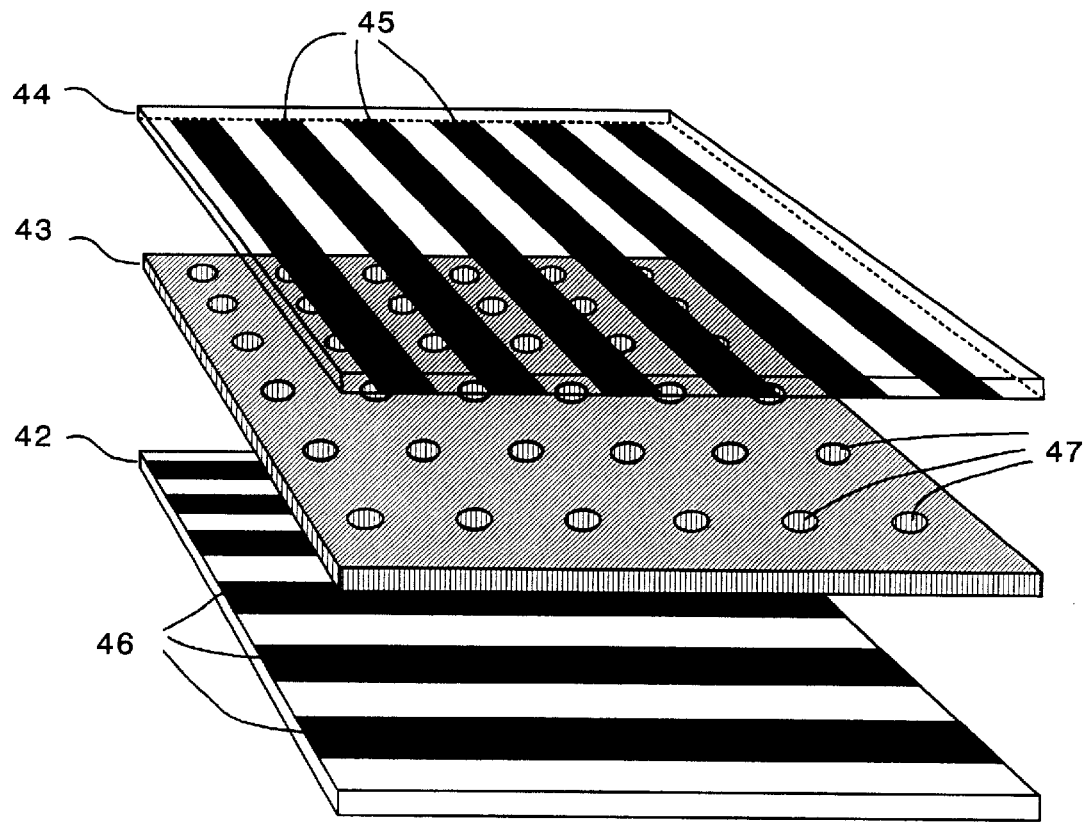
FIG. 10a is a surface pressure sensor is as 1a—exploded view.

FIGS. 10a and b show a further application of an elastic body with a number of integrated switches. The body comprises three thin elastic panels (42), (43) and (44). For purposes of elucidation, FIG. 10a shows an exploded view of these panels and (44) as a phantom view. In their real structure however, they lie one on top of the other and are joined to form one body. Thin metal coatings are vacuum-applied to the top of panel (42) and bottom of panel (44). These coats are so thin that they follow slight deformations of the elastic body without breaking. The layers are structured into strip conductors (45) and (46) which are in turn at right angles to each other. The middle layer (43) has apertures (47) from top to bottom at exactly the points where two metal strip conductors of panels (42) and (44) cross.

Figure 10B:
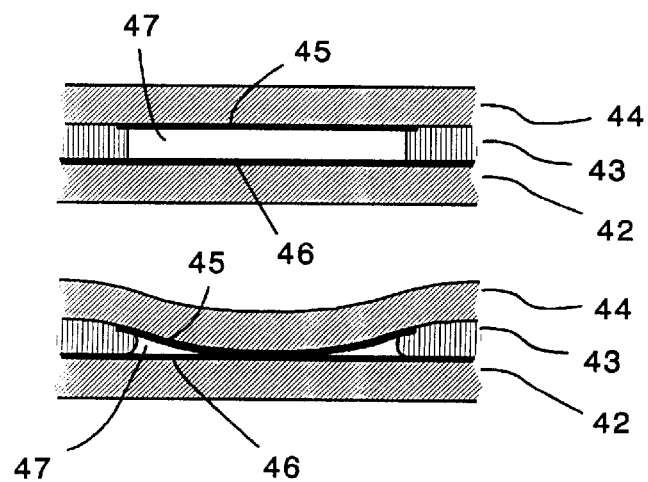
FIG. 10b is a figure like 10a except as a cross-section of a switch element.

If this type of elastic body lies on a firm surface—not shown here, that results in a switch at this position. This is clear from FIG. 10b, which shows the cross-section of such an aperture (47). In the top section of FIG. 10b, the two metal strips are separated by the height of panel (43), there is no electric contact. By pressing the top panel (44), the two strip conductors (45) and (46) make contact and the circuit is closed, lower section of FIG. 10b. Corresponding ventilation ducts of the apertures (47) are not shown here.

By knowing the locations of the apertures (47), this type of elastic body can be used for locally resolved pressure measurement. Such sensory matrices can for instance be located on the fingertips of the robot hand shown in FIG. 5 for the purpose of locally resolved touching. A more exact pressure resolution can be achieved by placing several sensory matrices one over the other. By using corresponding actuators, which could take e.g. the form of spiral springs (41), the touch result thus determined could be transmitted to the fingertip of the human finger (37) in the data glove shown in FIG. 9.

Figures 22A, 22B:
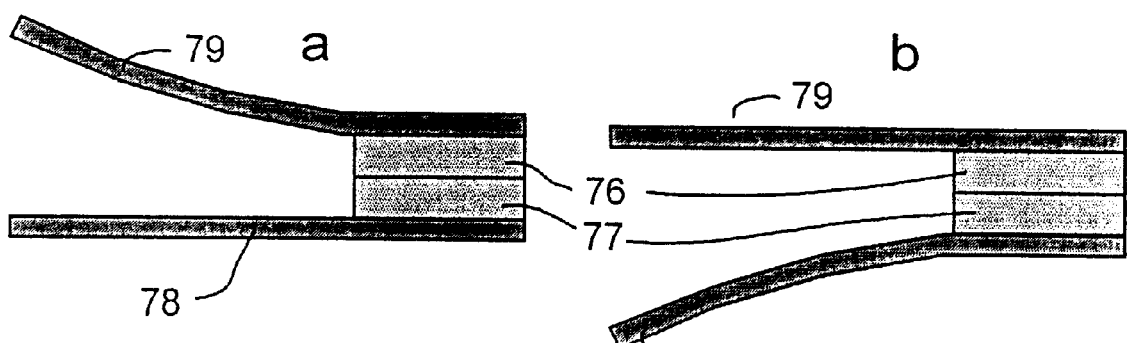
FIGS. 22a and B are cross-sectional views of memory actuators in different states.

FIG. 22a shows the actuator of claim 21 in its normal position and FIG. 22b in its acting state. When a peltier-element is heated the upper part 76 will cool down while the lower part 77 is heating up.

Figure 11:
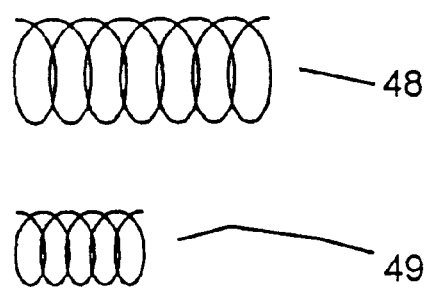
FIG. 11 are actuators made as springs out of shape memory metal.

The actuators can be different in their actuating characteristics. In FIG. 11 there are shown two spring-sme-actuators 48 and 49 different in size and with a different number of windings. Therefore, they will have a different characteristic of their actuating result.

Figure 12:
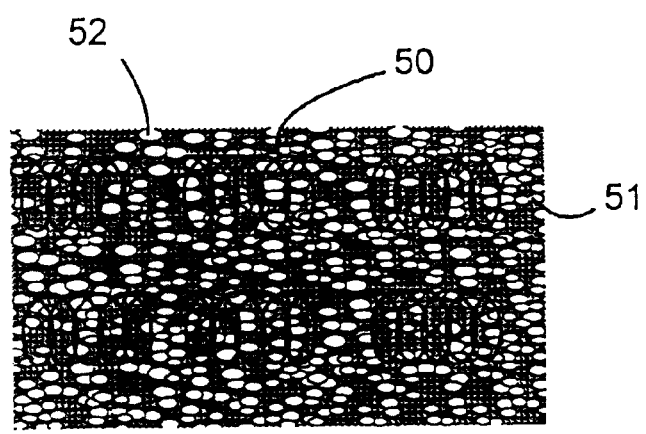
FIG. 12 are actuators inserted into foamed rubber.

If the springs 50 in FIG. 12 are inserted into a foamed rubber or foamed plastic material 51 they will deform the elastic material 51 more easy. Because of the holes 52 there is less repulsive force.

Figure 13:
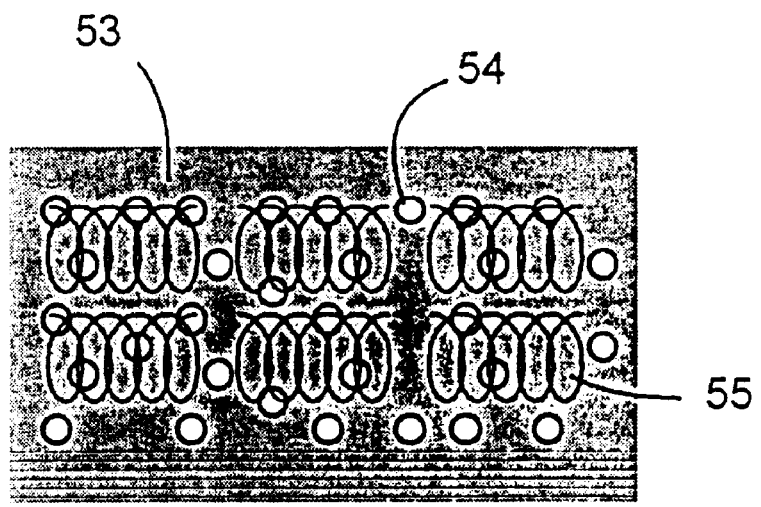
FIG. 13 are actuators inserted into elastic material with holes.
Figure 14:
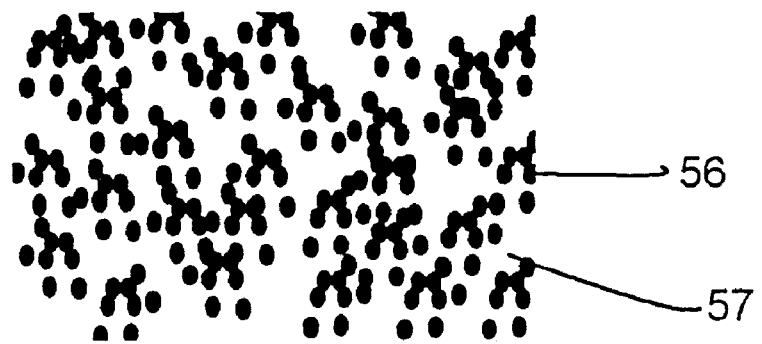
FIG. 14 are conducting particles inserted into the elastic material.
Figure 15:
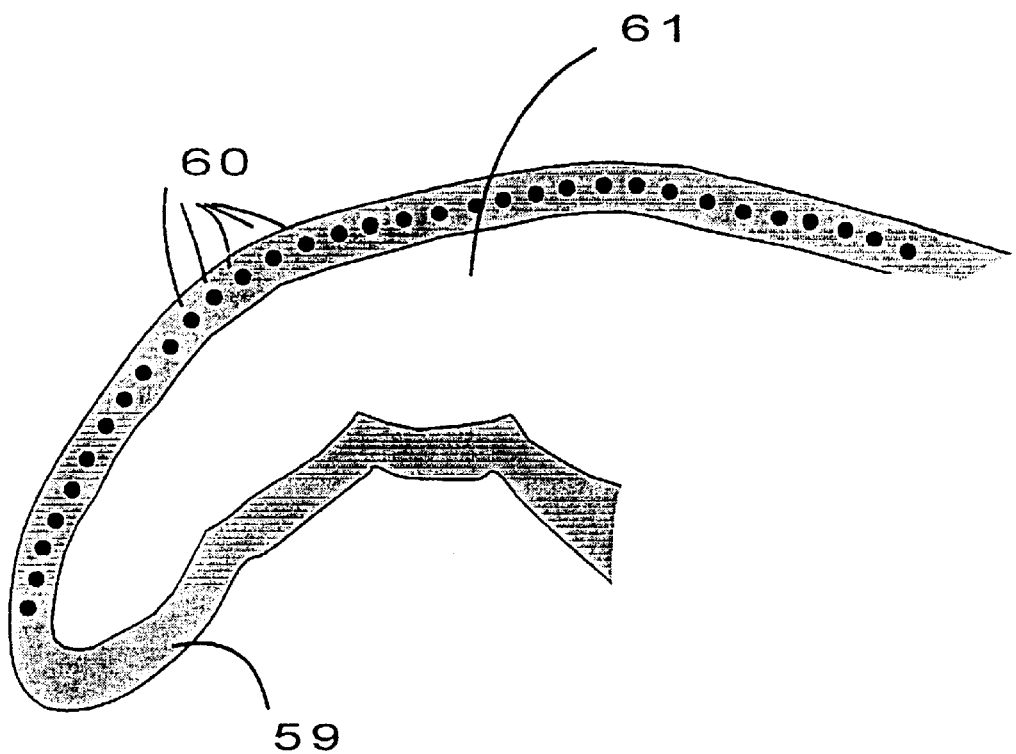
FIG. 15 is a cross-section of a finger of a glove for measuring the movements of the human fingers by resistance.
Figure 16:
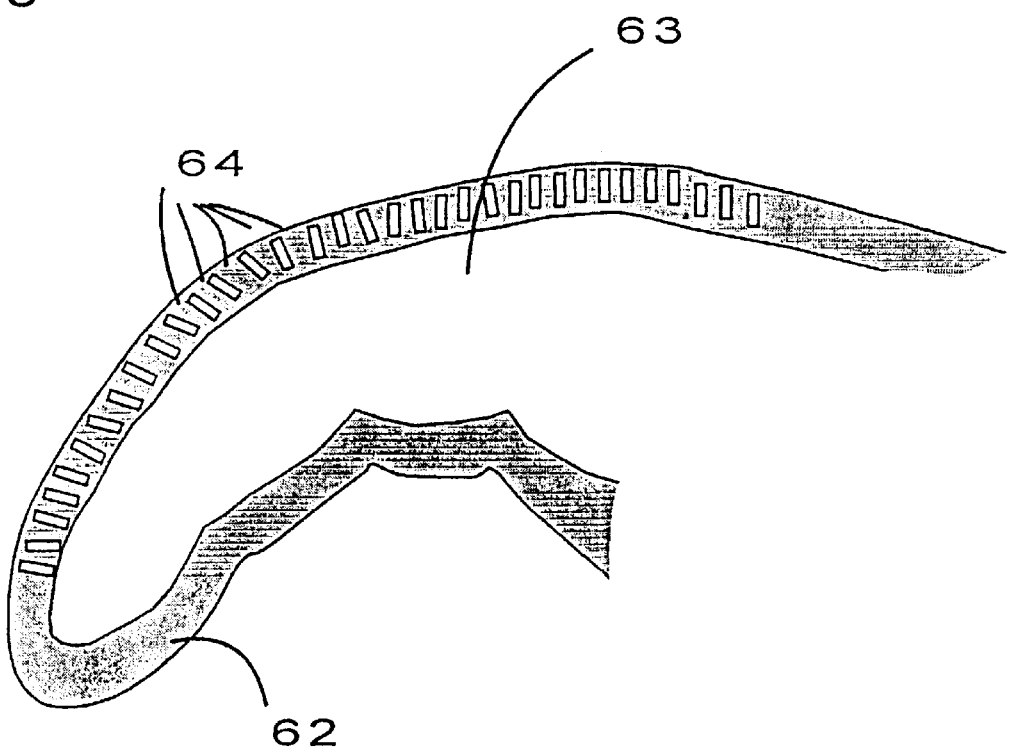
FIG. 16 is a cross-section of a finger of a glove for measuring the movements of the human fingers by capacitance.
Figure 17:
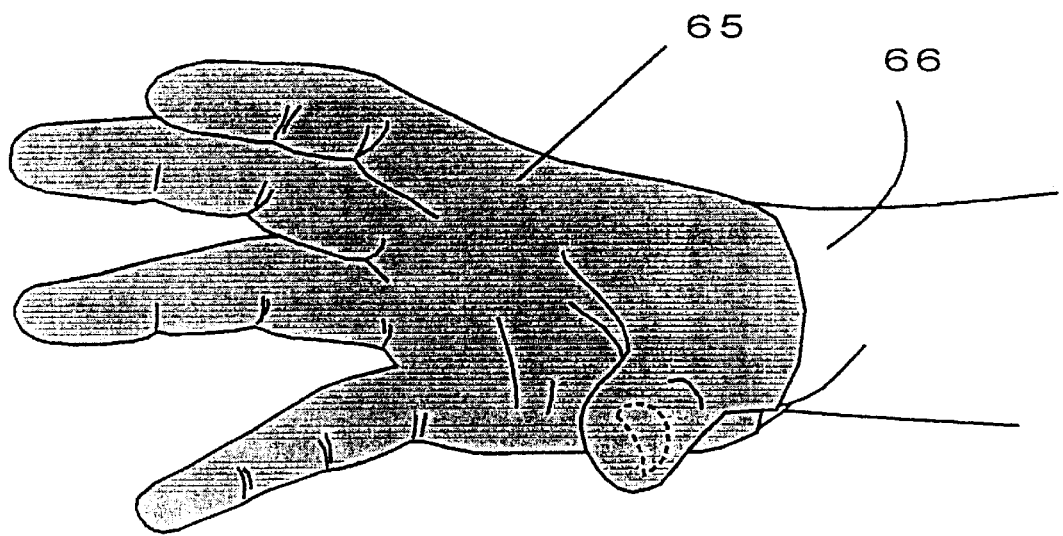
FIG. 17 is a view of a glove for measuring the movements of the human fingers and the hand for inserting the data into a computer.
Figure 18:
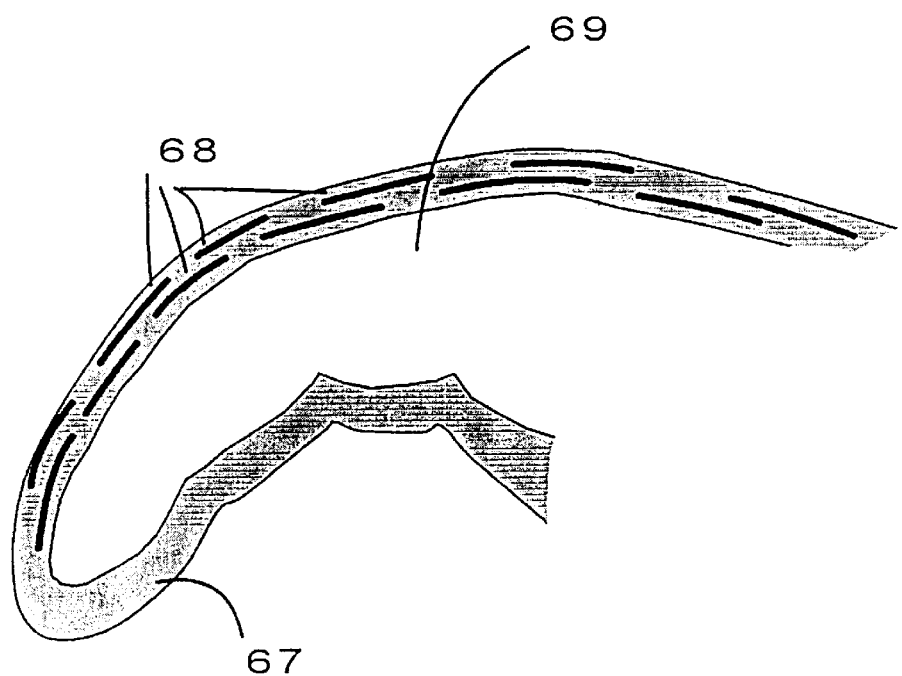
FIG. 18 is a cross-section of a finger of a glove for measuring the movements of the human fingers by strain gauge devices.

Also there can be defined holes 54 in the elastic material 53 giving the same result as the foamed material, as shown in FIG. 13. These holes may be inserted by bubbling a gas into the material while it is vulcanizing. To prevent people of seeing such a material, as described in FIGS. 12 and 13, it can be covered by a rubber film.

The glove 65 for measuring the movements of the hand 66, described in FIG. 9, can be used for virtual reality of software. One way of making such a glove is to insert electrodes 60 into a resistive material 59 and measure the change of resistance between next or other electrodes while the fingers 61 are moving. Because the resistance of the material depends of inner strain and stress of said material, the measurement result will be different. The resistivity of the rubber material can be defined by inserting conductive particles 56, powders or pastes into said rubber-material 57.

Another way of measuring the movement of the finger 63 is to insert electrodes 64 into the elastic material 62 and measure the capacitance between next electrodes. If the finger 63 is moving, the material 62 between said electrodes 64 will bend and change the distance of the electrodes 64. The result of this change in distance is a change in measured capacitance.

Figure 19:
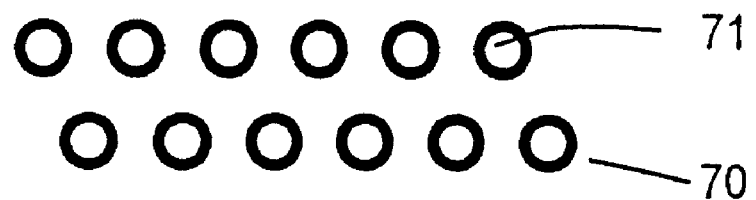
FIG. 19 is a cross-sectional view of a wire actuator.

FIG. 19 shows a cross-section of wire spring actuator 70 made out of tubes of shape-memory metal. Cooling liquid may be allowed to pass within tubes 70 and 71 to cool the metal and cause it to retract. Heating is accomplished applying current to the coil itself.

Figure 20:
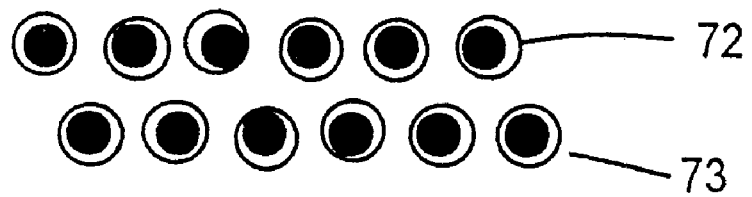
FIG. 20 is a cross-sectional view of another wire actuator embodiment.

FIG. 20 illustrates an alternative embodiment for the actuator, where the spring 73 is surrounded in this case by a cooling hose 72.

Figure 21:
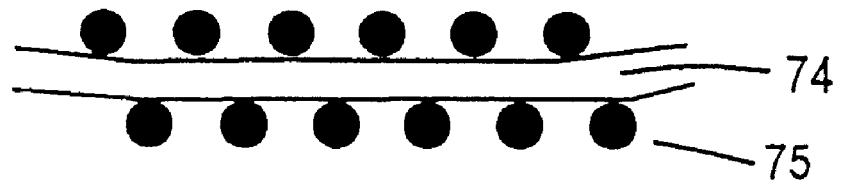
FIG. 21 is a cross-sectional view of another wire actuator embodiment with coolant.

In FIG. 21, the wire is hollow as well and the cooling hose 74 is located inside the wire 75.

All shape-memory actuators are preferable heated by direct current. A typical memory metal is Nitinol (Reg TM) of the metal NiTi. Alternatives are CuZnAl made of copper, which have a very low resistivity which is advantageous because of the use of high current heating.

Another way of constructing an actuator is with peltier elements 76 and 77 in FIG. 22, between two shape-memory metals plates 78 and 79. By selecting the steady state position of the actuator as shown in FIG. 22a, when the plates are heated, the position of 22b is achieved, i.e., that the plate 79 becomes flat and plate 78 now curves away therefrom. Thus, with a single electrical actuation (heating) the total actuation travel can be essentially doubled.

The interconnection of the physical wiring from the actuators (or sensors) and the computer is accomplished as shown in FIGS. 23a and b. The wires 80 are inserted into the elastic material 79 without being under strain so that they do not disconnect under movement.

Another type of actuator is shown in FIGS. 24a and b where part 81 of an elastic body with an actuator made of a balloon 85 contains a liquid 82 (such as water or other liquid with a boiling point under about 100° C.). The balloon 85 is attached to heating unit 84. If the liquid temperature exceeds the boiling point, it will change into a gas 83, which in turn increases its volume, and forces the elastic material 81 to reshape.

Another way of measuring the movements of the finger 69 is to insert a number of narrow spaced strain gauge devices 68 or any other pressure sensors which can be made small into the material 67. If the finger 69 bends, the strain gauge devices will bend as well and the output signal of such will change. The switches and sensors described in here may not show the same output characteristic.

A method for remote controlling a robot limb is to build the robot limb as an elastic body according to FIG. 5. A master part could comprise the identical shape. The master part could be made as an elastic body where switches or sensors are inserted. To operate the robot hand the operator would have to move the master part by its own human hands. A computer would adjust the robot hand in the desired position. The computer could do this by using a neuronal net.

One method for remote controlling a robot hand is that both, the operator's and the robot hand are wearing identical gloves, as described above with the help of FIGS. 8, 9, 15 to 18. The controlling of the movement of the robot hand is then done by simply adjusting the robot hand until the states where both gloves are identical.

What is claimed is:

1. A shapeable elastic body comprising:
   an elastic material;
   a plurality of narrowly spaced actuators embedded in said elastic material;
   a switch to activate said actuators individually or in groups; and
   a plurality of narrowly spaced sensors integrated into said elastic material;
   wherein the shape of said shapeable elastic body is the result of a summation of the state of activation of said actuators and at least one of said spaced sensors changes state when said shapeable elastic body changes shape.

2. An elastic body according to claim 1, wherein said actuators are configured in a two-dimensional actuator matrix embedded in said elastic material.

3. An elastic body according to claim 2, wherein said elastic body comprises two or more two-dimensional actuator matrices embedded in said elastic material.

4. An elastic body according to claim 1, wherein said elastic body is in the shape of a limb to form an elastic robot limb.

5. An elastic body according to claim 4, wherein a portion of said actuators comprise
   a balloon element;
   a liquid sealed within said balloon; and
   a means for heating said liquid to a gaseous state wherein activation of said means for heating heats said liquid sealed within said balloon to a gaseous state causing said balloon to expand to a larger volume.

6. A shapable elastic body according to claim 1, wherein said shapable elastic body is a lid having a peripheral edge for use with a container, wherein said actuators of said lid are remotely controllable for operating said actuators to lift said lid from said container and to seal said container in response to signals to said actuators.

7. A shapable elastic body according to claim 6, wherein said container includes a lip and wherein said lid includes actuators at said peripheral edge of said lid such that said lid can engage said lip in response to said signals to said actuators to cause tight engagement of said lid and container.

8. A shapable elastic body according to claim 7, wherein said tight engagement is further provided by actuators in said lid to wrap said peripheral edge of said lid around said lip.

9. An elastic body according to claim 4, wherein said actuators comprise materials having shape memory effect, said materials including thermo-metal-combinations or are working in an electromagnetic piezoelectric magnostrictive or electrostrictive way.

10. An elastic body according to claim 4, wherein a portion of said actuators comprise materials having a memory effect, said materials include electromagnetic materials.

11. An elastic body according to claim 4, wherein a portion of said actuators comprise materials having a memory effect, said materials including piezoelectric materials.

12. An elastic body according to claim 4, wherein a portion of said actuators comprise materials having a memory effect, said materials including magnostrictive materials.

13. An elastic body according to claim 4, wherein a portion of said actuators comprise materials having a memory effect, said materials including electrostrictive materials.

14. An elastic body according to claim 4, wherein a portion of said actuators are springs formed out of shape memory metal.

15. An elastic body according to claim 4, wherein said elastic material is foamed rubber.

16. An elastic body according to claim 4, wherein said elastic robot limb is the shape of a hand.

17. An elastic body according to claim 4, wherein said elastic robot limb comprises the shape of a body part.

18. An elastic body according to claim 9, wherein said actuators include a pair of peltier-elements first and second plates capable of bending in response to a change in temperature and means for heating said plates to change their temperature, and wherein said first plate is generally flat and said second plate is generally curved away from said first plate at one end thereof, and when said plates are heated, said first plate becomes generally flat and said second plate curves generally away from said first plate at one end thereof.

19. An elastic body according to claim 9, wherein said actuators include plates of shape-memory material and include resistors mounted on said actuators to transmit heat thereto.

20. A elastic body according to claim 4, wherein said actuators are plates formed out of shape-memory material having a peltier-element in-between them, such as the one bends down when the upper part of the peltier-element cools and one bends down when the lower part of the peltier-element heats up and visa versa.

21. An elastic body according to claim 4, wherein said elastic robot limb comprises said actuators, wherein said actuators are plates out of shape-memory material and that resistors designed as surface mounted devices are mounted on said actuators to heat these actuators.

* * * * *